(12) United States Patent
Jensen et al.

(10) Patent No.: US 7,234,860 B2
(45) Date of Patent: Jun. 26, 2007

(54) DYNAMIC DEW POINT ANALYSIS METHOD AND A DEVICE FOR DETERMINING THE DEW POINT TEMPERATURE AND RELATIVE HUMIDITY

(75) Inventors: Ole Mejlhede Jensen, Holte (DK); Per Freiesleben Hansen, deceased, late of Solrød Strand (DK); by Kirsten Højst Hansen, legal representative, Solrød Strand (DK)

(73) Assignee: Aalborg Universitetet, Alborg (DE)

( * ) Notice: Subject to any disclaimer, the term of this patent is extended or adjusted under 35 U.S.C. 154(b) by 54 days.

(21) Appl. No.: 10/495,984

(22) PCT Filed: Nov. 18, 2002

(86) PCT No.: PCT/DK02/00773

§ 371 (c)(1),
(2), (4) Date: Dec. 7, 2004

(87) PCT Pub. No.: WO03/044510

PCT Pub. Date: May 30, 2003

(65) Prior Publication Data

US 2005/0152431 A1    Jul. 14, 2005

(30) Foreign Application Priority Data

Nov. 20, 2001  (DK) .................... PA 2001 01725

(51) Int. Cl.
*G01N 25/02* (2006.01)
(52) U.S. Cl. .................... 374/28; 374/16; 374/45
(58) Field of Classification Search .......... 374/28, 374/109, 20, 16, 17, 43, 32, 45
See application file for complete search history.

(56) References Cited

U.S. PATENT DOCUMENTS

| 3,396,574 | A |   | 8/1968  | Hanlein et al. |
|-----------|---|---|---------|----------------|
| 4,523,860 | A | * | 6/1985  | Chin et al. ..................... 374/27 |
| 4,579,462 | A | * | 4/1986  | Rall et al. ..................... 374/28 |
| 4,906,105 | A | * | 3/1990  | Geake .......................... 374/30 |
| 5,816,704 | A | * | 10/1998 | Campbell et al. ............. 374/28 |
| 6,202,480 | B1| * | 3/2001  | Mauze et al. .................. 73/77 |
| 6,257,757 | B1| * | 7/2001  | Nakamura ................... 374/14 |
| 6,390,669 | B1| * | 5/2002  | Nakamura et al. ............ 374/12 |
| 6,470,289 | B1| * | 10/2002 | Peters et al. ................. 702/132 |
| 6,575,621 | B1| * | 6/2003  | Zlochin ....................... 374/28 |
| 6,921,195 | B2| * | 7/2005  | Pipe et al. .................... 374/43 |

FOREIGN PATENT DOCUMENTS

| EP | 0538910 | 4/1993 |
| GB | 2190203 | 11/1987 |

* cited by examiner

*Primary Examiner*—Diego Gutierrez
*Assistant Examiner*—Megann E. Vaughn
(74) *Attorney, Agent, or Firm*—James Creighton Wray

(57) ABSTRACT

The invention provides for a dynamic dew point analysis method as well as an apparatus for carrying out the method wherein the method comprises: arranging a moisture containing gas in the immediate vicinity of at least two thermocouples, where one thermocouple is shielded from the gas; creating an analogous temperature change in both thermocouples and registering the temperature in both thermocouples during a cycle where the condensation point of the moisture containing gas is passed, using the different temperatures from the at least two thermocouples as input for determining the dew point according to basic thermodynamic principles.

8 Claims, 6 Drawing Sheets

DYNAMIC DEW POINT ANALYSIS METHOD AND A DEVICE FOR DETERMINING THE DEW POINT TEMPERATURE AND RELATIVE HUMIDITY

This application claims the benefit of Danish Application No. 2001 01725 filed Nov. 20, 2001 and PCT/DK02/00773 filed Nov. 18, 2002.

BACKGROUND OF THE INVENTION

The present invention relates to a dynamic dew point analysis method as well as a device for determining the dew point temperature and relative humidity.

In the art a number of different methods and devices have been suggested in order to determine the relative humidity as well as the dew point temperature. Among these is for example an optical system arranged in connection with a mirror or other reflective surface. By projecting a light beam and measuring the reflection from the light-reflecting surface the time when the light reflection diminishes due to condensation on the light-reflecting surface can be determined and the temperature corresponding to that time/instant is recorded whereby the dew point temperature has been determined. With this temperature the relative humidity in the vicinity of the reflective surface can be calculated.

In older measuring devices hair from a horsetail was used as the hair will expand/contract due to changes in the relative humidity. Also in modern times devices have been designed for registering the changes of moisture in the atmosphere. One such sensor is known from Remote Measurement Systems Inc. where a thin gold-plated plastic film transducer is used. As the moisture in the atmosphere changes, the capacitance of the film will change. The output from the sensor is an electrical signal which can be converted by known means to a read-out in a display. Due to certain physical limitations this measuring device is only suitable in the range from 10% to 90% relative humidity.

SUMMARY OF THE INVENTION

Relative humidity is the ratio of the current absolute humidity to the highest possible absolute humidity. The amount of humidity in the air depends on the current air temperature. A reading of a 100% relative humidity means that the air is totally saturated with water vapour and cannot hold any more, creating the possibility of for example rain. As the temperature in the air or a moisture containing gas drops, the point of saturation, also called the dew point, will eventually be reached, depending on the relative humidity in that air/gas. It is the object of the present invention to provide a new method for measuring equilibrium relative humidity and equilibrium dew point temperature.

This done by a new method called dynamic dew point analysis (DDA). Compared to other methods used today, the developed dew point meter permits a quick and very accurate measurement of the equilibrium relative humidity. The dynamic dew point analysis technique should be of interest for individuals or companies working with measurement or control of the moisture content, especially for materials in the course of research or for industrial purposes.

The invention does provide for a dynamic dew point analysis method wherein the method comprises:

arranging a moisture containing gas in the immediate vicinity of at least two thermocouples, where one thermocouple is shielded from the gas;

creating an analogous temperature change in both thermocouples and registering the temperature in both thermocouples during a cycle where the condensation point of the moisture containing gas is passed, using the different temperatures from the at least two thermocouples as input for determining the dew point according to basic thermodynamic principles.

Furthermore, the invention discloses a device for determining the dew point temperature as mentioned above which is special in that it comprises a device for determining the dew point temperature and relative humidity, wherein the device comprises a housing and that at least two thermocouples are provided inside said housing wherein at least a part of the interior of the housing constitutes a measuring chamber, and that one of the at least two thermocouples is shielded from exposure to the measuring chamber; that means are provided for changing the temperature of the thermocouples and registering the temperatures and/or the temperature difference between the at least two thermocouples.

The basic principle of the DDA-measurement is to record the momentary shift of the thermal boundary condition of a sensor surface arising when the surface is cooled to a temperature that is below the dew point temperature of the surrounding air. When the dew point temperature is passed, the heat transfer is changed from being purely convective to being a coupled heat-moisture transfer, where the convective contribution is superposed by a condensation-bound phase transformation. The effect of this shift of boundary condition is partly restrained in humid atmospheric air at room temperature, since the contribution from the phase transition is diffusion controlled. If, on the other hand, the shift of thermal boundary condition occurs in an evacuated system, the condensation rate is determined by a water vapour flow due to pressure differences in the system. This will cause a drastic increase of the thermal transfer potential. In this system the dew point temperature therefore becomes a very precise and distinct physical phenomenon.

As a measuring technique DDA makes it possible to determine the dew point temperature $T_d$—and thus the relative humidity RH—in a closed system by dynamic passage of the dew point temperature, $T_d$. The principle, therefore, deviates fundamentally from the methods for dew point determination used so far, according to which a static moisture equilibrium is preserved for example on a condensation surface by controlling the optical light reflection of the surface.

In a further advantageous embodiment of the invention the measuring chamber is completely sealed up from the surrounding environment and a source of vacuum may be connected for evacuating the measuring chamber.

This embodiment is especially useful when the device is used for determining the moisture content of materials for research or industrial purposes where a sample of the material can be arranged inside the measuring chamber. Further, by evacuating the atmosphere, i.e. air that was present when the measuring chamber was sealed off, it is ensured that the moisture in the measuring chamber derives from the material sample placed in the measuring chamber. As the condensation occurs on the exposed thermocouple, this will then be a measure for the moisture content in the material sample.

In a further advantageous embodiment a thermocouple is provided for measuring the temperature of the housing. A correlation between the temperature of the housing and the test sample has been established. In a preferred embodiment of the invention the test sample is placed in a container made from a heat conducting material, as for example copper. In this instance the temperature of the sample is equal to the temperature as measured by the thermocouple in the housing. This is done in order to be able to compensate for the heat/cooling contribution by the housing material on the conditions inside the measuring chamber.

In a further advantageous embodiment the thermocouples are arranged in a member exhibiting low thermal conductivity such as a plastic member so that only the tips of the thermocouples are exposed to the measuring chamber of which one thermocouple is shielded. The member constitutes an isolating member so that the thermocouples are isolated from a source of heat or cooling which could otherwise influence the measurements. By only exposing the tips of the thermocouples, which can have a very limited area, for example 0.25 mm$^2$, it is possible to determine the temperature change very accurately. As one thermocouple is shielded, for example by covering the tip of the thermocouple with a cap, and not covering the other thermocouple, the conditions surrounding the thermocouples are basically equal, so it will be assured that only the condensation and the change in temperature on one thermocouple are the phenomena which are actually measured by the two thermocouples.

In a further advantageous embodiment of the invention the side of the member exhibiting low thermal conductivity such as a plastic member not being exposed to the measuring chamber, the thermocouples are encased in a heat-conductive material for example copper, and that a heating and/or cooling element is arranged in connection with the encasing. In this manner, for example by providing a peltier cooling element it will be possible to induce a dynamic temperature lowering of the plastic element and the thermocouples. As the thermal diffusivity of the plastic element, for example being made from epoxy, is approximately $10^{-7}$ m$^2$/second and for copper $10^{-4}$ m$^2$/second, i.e. a factor of 1000 difference, the temperature drop induced by the peltier element will almost exclusively be transferred through the copper wire to the tip of the thermocouple. The temperature lowering is therefore very effectively brought forward to the measuring points of the exposed and shielded thermocouples without significant temperature lowering of the surrounding plastic surface.

The peltier cooling element is used to, in a controlled manner, induce the dynamic temperature lowering so that the tip of the thermocouple will pass the dew point temperature whereby condensation on the tip of the thermocouple will occur.

In a further advantageous embodiment of the invention the housing is made of two mutually fitting sections which can be fitted in such a way that the measuring chamber, thermocouples, member exhibiting low thermal conductivity such as a plastic member, encasement and heating/cooling elements are comprised inside the housing and that means are provided through the housing for connecting the thermocouples to registering means and the heating/cooling elements to control means and optionally the measuring chamber to a source of vacuum.

This embodiment is especially suitable for use in laboratories on site or in other situations where it is desirable to place a sample of a material inside a measuring chamber where all boundary conditions can be controlled.

In a still further advantageous embodiment the device comprises means for creating a dynamic gas flow around the thermocouples and the housing is in open communication with the surrounding environment. With this embodiment of the invention it is possible, by means of a ventilator or other means for creating a dynamic gas flow around the thermocouples to monitor the dynamic dew point of air in a room or outside. The heating and/or cooling elements provided in connection with the device may in this embodiment be pre-programmed in such a way that when the dew point is registered, the thermocouples will be heated to a temperature above the dew point temperature whereafter a new cooling cycle can be initiated. In this manner it becomes possible within short time intervals to register the dew point temperature.

In a further advantageous embodiment the device is a self-contained unit comprising a source of power, means for registering, storing, computing, and displaying the measurements. Especially for field applications or other not so permanent installations it is advantageous that the device itself is fully self-contained.

The invention will now be explained in more detail with reference to the accompanying drawing wherein

DETAILED DESCRIPTION OF THE PREFERRED EMBODIMENTS

Figure 1:
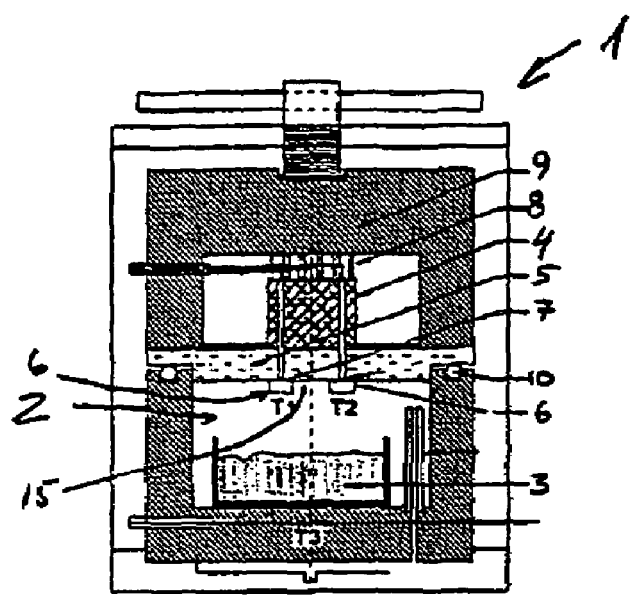
FIG. 1 illustrates a schematic cross-section of the dew point meter.
Figure 2:
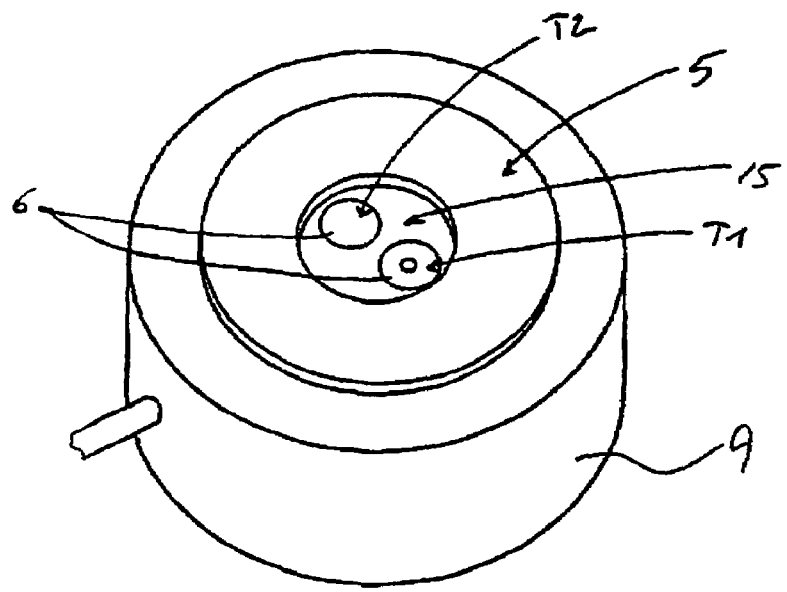
FIG. 2 illustrates details of the centre unit.

A schematic cross section of the dew point meter 1 is shown in FIG. 1, and the dew point meter is shown in FIG. 2 together with details of the sensor surface.

The illustrated dew point meter comprises an outer casing 9 made from for example aluminium. The casing is in two parts and a seal 10 is fitted in the connecting section of the casing 9. The measuring chamber 2 arranged inside the device 1 contains the sample 3 to be tested. The measuring chamber 2 is evacuated so that the atmosphere is pure water vapour in equilibrium with the sample.

The bottom side of the sensor unit is equipped with two type-T thermocouples (copper/constantan), marked T1 and T2, respectively. The location of these thermocouples is shown in detail in FIG. 1. The thermocouples are electrically isolated from, but in intimate thermal contact with, a copper block 4. The thermocouples extending from the copper block 4 are embedded in a thermoset plastic element 5. The thermocouples are composed of Ø 0.2 mm wires welded together at the sensor point; the weld forms a spherical sensor point. After embedment of the thermocouples the thermoset plastic surface 15 is ground and polished so that the sensor surface consists of a plane, circular and polished metal surface. The resulting sensor surface has an area of 0.25 mm². If the thickness of the plastic layer 5 is chosen so that the thermal resistance through the thermocouple wire and the convective transfer resistance are of equal magnitude (Bi≈1), maximum sensitivity by shift of boundary condition is attained.

Two caps 6 are placed on top of the sensor surfaces; the cap 6 covering sensor T1 is equipped with an opening and the other cap covering sensor T2 is gas-proof. Thus, the sensors have almost identical thermal boundary conditions with regard to heat conduction and convection. At the same time, condensation can only take place on the sensor surface of T1, which then becomes the active condensation sensor 7.

In the DDA technique it is utilised that thermocouples can measure temperature differences very accurately (≈0.001° C.), whereas an absolute temperature measurement with electronic reference is less accurate (≈0.1° C.). The thermocouples are coupled to measure the differential temperature dT1.2 between sensor T1 and sensor T2, and the differential temperature dT1.3 between the active sensor T1 and the temperature of the sample T3. At the same time the absolute temperature of the tested sample T3 is measured. A central point in the DDA technique is that the uncertainty in the absolute temperature of the sample T3 does not influence the measuring accuracy of the dew point or the RH. This is dominated by the dT1.3 determination, which is a very accurate differential temperature measurement.

During measuring the copper block 4 surrounding the sensors T1 and T2 is cooled by a peltier element 8. This induces a dynamic temperature lowering of the plastic element 5 and the thermocouples T1, T2. The thermal diffusivity, however, is about $10^{-7}$ m²/s for epoxy and about $10^{-4}$ m²/s for copper, i.e. a factor of 1000 in difference. For this reason the temperature drop is almost exclusively transferred through the copper wire of the thermocouples T1, T2. The temperature lowering is, therefore, very effectively brought forward to the measuring points of the active and the passive thermocouples without significant temperature lowering of the surrounding plastic surface.

Figure 3:
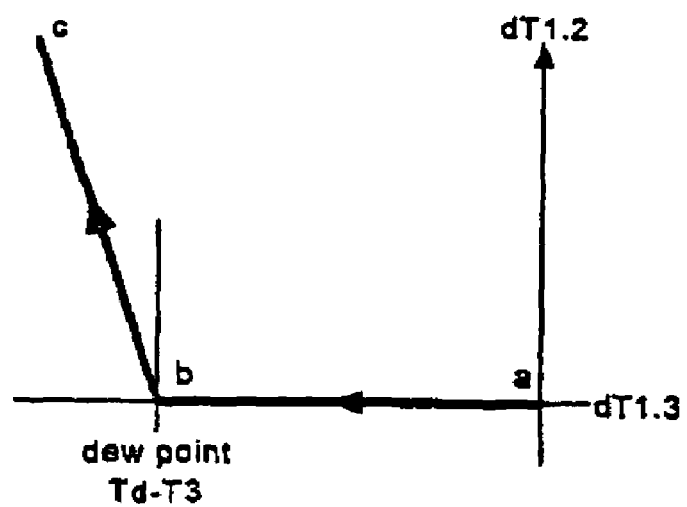
FIG. 3 illustrates a schematic DDA measuring course.

A temperature development as shown schematically in FIG. 3 is attained. The measurement starts in point a, and is terminated in point c. An easy identification of the dew point is enabled due to the distinct difference between the two curve sections: Base line (a–b) and condensation section (b–c). During cooling the temperature difference, dT1.2, between the active and the passive sensor T1, T2 will be close to 0° C. on the curve a–b with convective heat transfer at the surface. As the dew point temperature is passed, i.e. when dT1.3=Td–T3, the heat transfer shifts from being purely convective to being a coupled moisture-heat transfer, where the convective heat transfer is superposed by an exothermic, condensation-bound phase transformation. This results in a well-defined change of the b–c curve for the differential temperature, dT1.2, as shown in FIG. 3.

Figure 4:
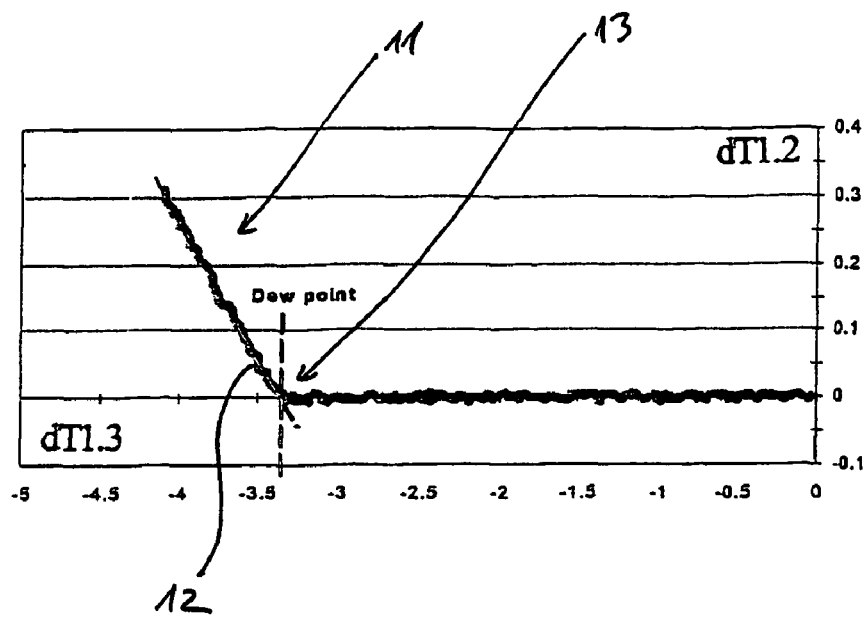
FIG. 4 shows an example of a single measuring sequence.
Figure 5:
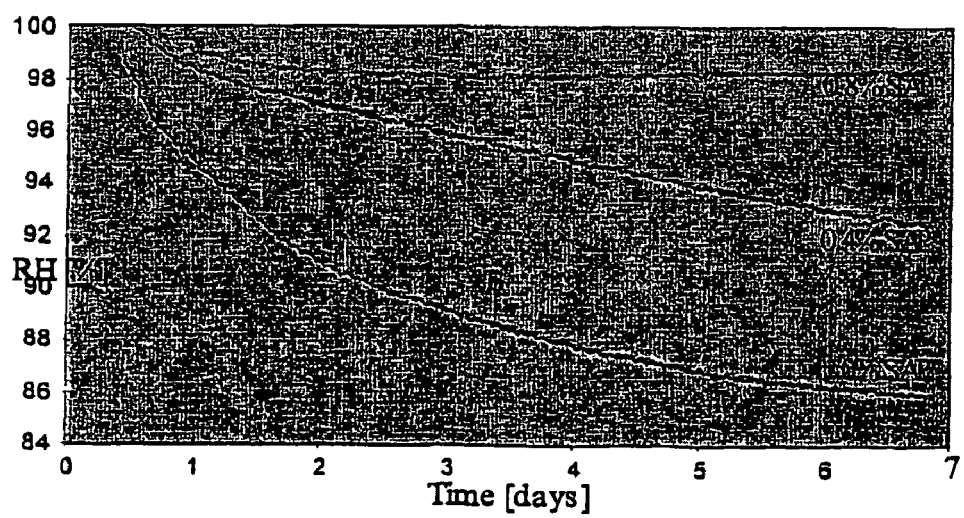
FIG. 5 shows the results of a series of measurements on a hydrating cement base.

FIG. 4 shows an example of a single measuring sequence using the DDA technique, and FIG. 5 shows the result of a series of measurements on a hydrating cement paste. In FIG. 4 an example of DDA measurement on a cement paste sample at 20° C. According to back extrapolation of the linear condensation section the dew point is reached at a temperature depression of 3.33° C. This corresponds to an ERH of approximately 81% for the material sample. The duration of the shown measuring course is about 5 minutes with the prototype in use. The cooling cycle is terminated when a differential temperature dT1.2 of approximately 0.35° C. is reached. The condensation part 11 of the curve is approximated by linear regression in the range 0.1° C.<dT1.2<0.3° C. as illustrated by dashed line 12, and the point of deviation 13 is subsequently determined by back extrapolation of this line. Based on this the dew point temperature and the relative humidity can be calculated. Note that the point of deviation 13 determines the dew point temperature, Td, at a time where no vapour from the surroundings has condensed on the sensor surface. Technically this means that the interaction between sensor and sample is eliminated.

Up to dT1.2≈0.05° C. the condensation section is not fully linear. This soft slope transition is assumed to be due to poly-molecular surface adsorption of water vapour, however, verification of this still remains.

After the termination of the cooling cycle the copper block 4 is heated by the peltier element 8 to a temperature approximately 1.5° C. above the material sample 3 temperature. This prevents build-up of condensation on the sensor surface and allows measurement of ERH up to 100%.

In FIG. 4 small deviations from dT1.2=0 are observed for the base line. Random fluctuations are due to electrical noise and resolution of thermocouple measurements, and systematic deviations are due to thermal asymmetry between the two thermocouples: Size of thermocouple junction points, thickness of copper wires, thermal contact between copper wires and copper block etc. In the present set-up dT1.2 is less than approximately 0.01° C. for the base line and, therefore, negligible. In an earlier set-up no cap was used around the active thermocouple. This lead to a systematic base line skewness of 0.04° C., which, however, could be corrected for mathematically.

In FIG. 5, measurements of ERH every 20 minutes on three hydrating cement pastes with different additions of superabsorbent polymer, SAP is illustrated. The so-called autogenous RH-change is seen to be mitigated very efficiently by the SAP addition. The cement paste is mixed at time 0 with a water/cement ratio of 0.30 and with 20% silica fume addition.

In the present set-up a Campbell Scientific CR10X data logger (not shown) is used to control the cooling, heating, data processing and storage of data. The peltier cooling 8 is applied as pulses and controlled as to give a constant temperature lowering rate of, typically, 1.5° C./minute. It results in linear condensation sections of the DDA measuring courses, and enables simple and accurate back-extrapolation. A faster measuring cycle can be attained by increasing the cooling rate or by changing the thermal geometry of the T1 and T2 thermocouples; by using thicker copper wires or by shortening their length (thinner plastic element). A change of this kind may not lead to any significant loss of accuracy.

With the present design of the dew point meter relative humidity in the range 50–100% can be measured. The lower limit is confined by the cooling effect of the peltier element and the geometry of the thermocouple sensor. A simple increase in cooling effect of the present measuring system expands the measuring range to 25–100% RH. A further optimisation of the measuring system is expected to enable measurements down to approximately 10% RH.

For advanced laboratory use a data logger like the Campbell Scientific CR10X is sufficient for the dew point meter control since it is necessary for the data storage. However, for simple laboratory use and for field use an integrated circuit designed to perform the control and analysis of the measuring course may be used.

To simplify the laboratory use and especially to enable field use a separate evacuation tool may be used. A few strokes with a "converted" bicycle pump would is a simple and well-defined way to evacuate the measuring chamber—as shown below the evacuation does not need to be complete.

Testing of the DDA technique has mainly been carried out with saturated salt solutions and with a so-called two temperature generator.

Figure 6:
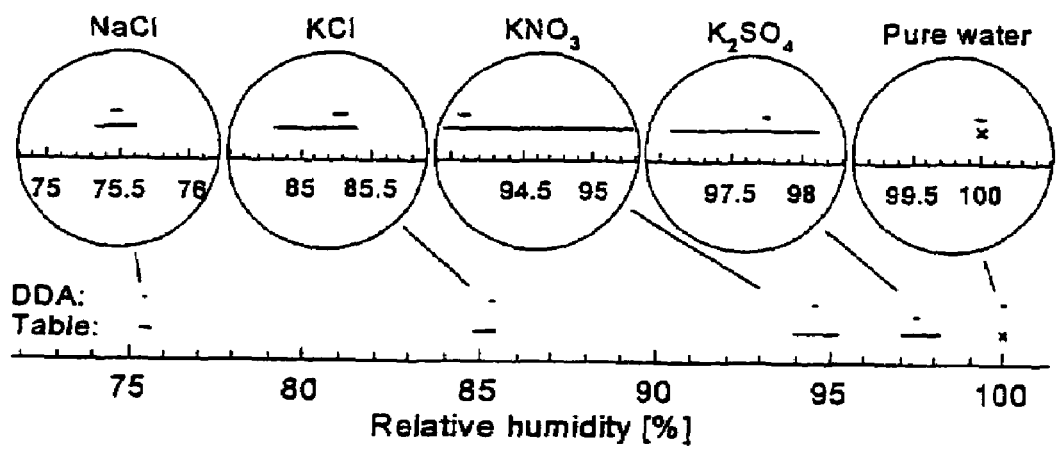
FIG. 6 illustrates comparison of DDA measurements and table data from the literature.

A series of measurements have been made with saturated solutions of NaCl, KCl, KNO$_3$ and K$_2$SO$_4$ and demineralised water. FIG. 6 shows DDA measuring results together with table data from the literature in particular Greenspan *Humidity fixed points of binary saturated aqueous solutions*, Journal of Research of the National Bureau of Standards—A. Physics and Chemistry, 81A, 1, January–February 1977, 89–96. As seen, the DDA measurements are in all cases in agreement with the literature data. Actually, these measurements indicate that the DDA technique is more accurate than known data values for saturated salt solutions.

Figure 7:
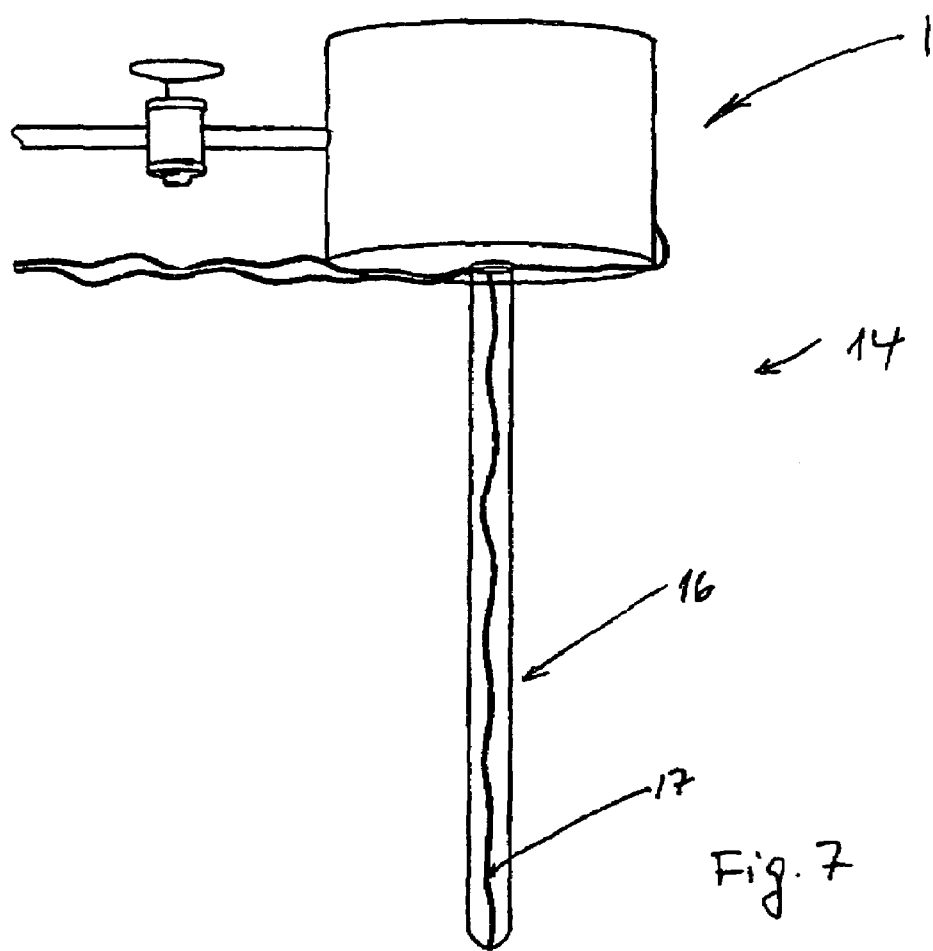
FIG. 7 illustrates a two-temperature generator.

The RHs generated by the saturated salt solutions shown above are not accurate enough to test the uncertainty of the DDA technique. For this reason a so-called two-temperature generator 14 was constructed, see FIG. 7. This method establishes a very accurate physical reference. The unit 14 consist of the DDA measuring chamber 1 with a glass tube 16 extending from the bottom. The glass tube 16 is in open contact with the measuring chamber 2 and closed in the bottom. A drop of demineralised water is placed in the bottom of the glass tube, and the glass tube is immersed into a thermostatically controlled bath. A thermocouple 17 in the water drop enables readings of the true dew point temperature, which can be compared with the dew point temperature measured by the Dew point Meter. During measurement the glass tube and the measuring chamber are evacuated.

Figure 8:
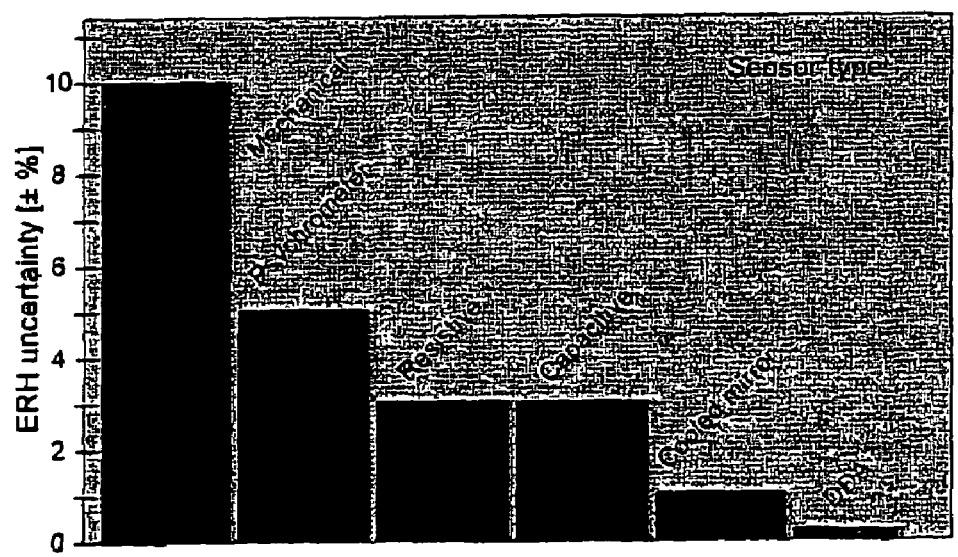
FIG. 8 illustrates the DDA results compared with the results of other measuring techniques.

This two-temperature generator 14 was used at an early time of the prototype development. At this stage it was concluded that the dew point determination with the constructed dew point meter was better than 0.05° C. The present prototype of the dew point meter indicates that the accuracy is around ±0.01° C. or approximately ±0.05% RH. In any case the DDA technique is much more accurate than other techniques, see FIG. 8.

When the sensor temperature passes the dew point temperature condensation of water vapour occurs on the sensor surface. The condensation rate is diffusion controlled, and therefore partly restrained, in atmospheric air. In an evacuated system, the condensation rate is determined by water vapour flow due to pressure differences in the system. This increases the condensation rate drastically.

Figure 9:
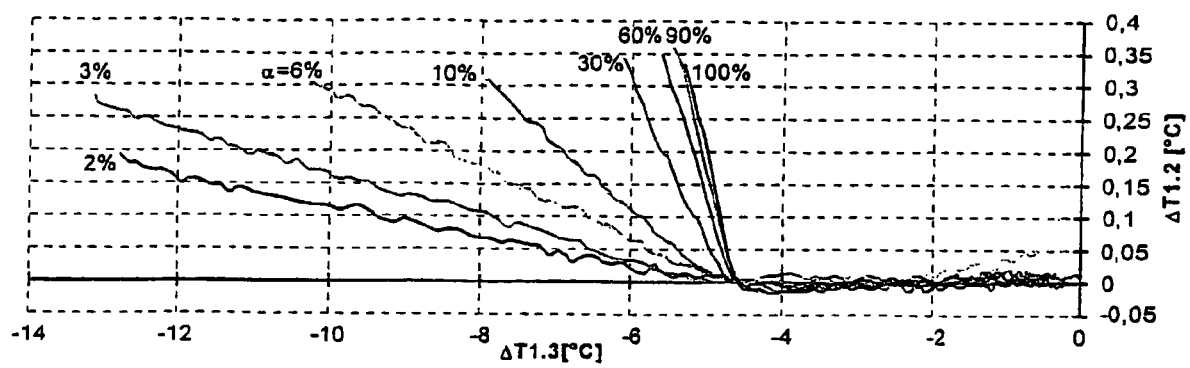
FIG. 9 illustrates the DDA measurements at different degrees of evacuation.

FIG. 9 shows measuring courses at different degrees of evacuation, expressed by the water vapour fraction, $$\alpha = \frac{p_w}{p_{tot}}$$

where $p_w$ is the water vapour pressure and $p_{tot}$ is the total pressure. Pure water vapour thus corresponds to $\alpha=100\%$. The experiments were performed at 20° C. with saturated NaCl, i.e. RH≈75%. At this condition atmospheric air has $\alpha=2\%$ (no evacuation).

A much more distinct response is observed in the evacuated measurements. These measurements were performed without a cap on the active sensor. An even more significant influence of the degree of evacuation is expected with a cap on the active sensor.

As shown in FIG. 9, evacuation of the measuring chamber 2 improves the measuring accuracy of the DDA technique. This initial evacuation results in unwanted moisture loss from the material sample 3. It is, however, possible to minimise and control this moisture loss. This is done by connecting the measuring chamber 2 to a pre-evacuated desiccator (not shown), with a volume approximately 100 times larger than the measuring chamber. When the two volumes are connected the pressure drop in the measure chamber 2 occurs very fast whereas moisture loss from the sample 7 is delayed relative to this.

With this procedure a connection time of 2 s ensured a fully sufficient evacuation of the measuring chamber. The moisture loss from the sample due to this evacuation procedure was measured to approximately 0.002 g, i.e. negligible.

During a DDA measurement water condenses on the sensor surface of the active thermocouple T1. This water is removed from the surrounding air and, potentially, also from the material sample 3. As previously mentioned, the dew point temperature is, in principle, determined at a time where no vapour has condensed on the sensor surface. It is, however, desirable that the water exchange between sensor and sample is as small as possible.

This phenomenon has been examined by comparison of differential sensor temperatures during condensation and during electrically induced heating. This experiment shows that at a differential sensor temperature of dT1.2=0.35° C. about 30 000 molecular layers of water is build up at the sensor surface. This corresponds to the water vapour in about 10 mm$^3$ of air at 100% RH, 20° C. or about 0.03% of the water vapour in the measuring chamber at 100% RH, 20° C. Consequently the interaction with the material sample 3 seems to be completely negligible.

Even the interaction with the chamber air is seen to be negligible. This was further confirmed by an experiment where measurements were preformed without a material sample: The empty measuring chamber was filled with water vapour at 75% RH and sealed. Subsequent measurements were performed with the same accuracy as with a material sample present.

Figure 10:
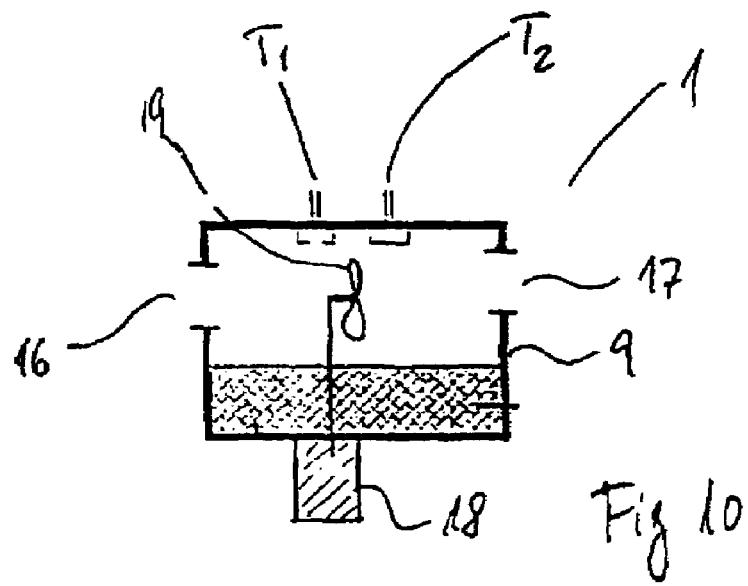
FIG. 10 illustrates a dew point measuring device with means for creating dynamic gas flow.

In FIG. 10 is illustrated a dynamic dew point measuring device 1, wherein an inlet opening 16 and an outlet opening 17 are provided in the casing 9, such that a dynamic gas flow by activating an electric motor 18, driving a ventilator van 19 is created.

Figure 11:
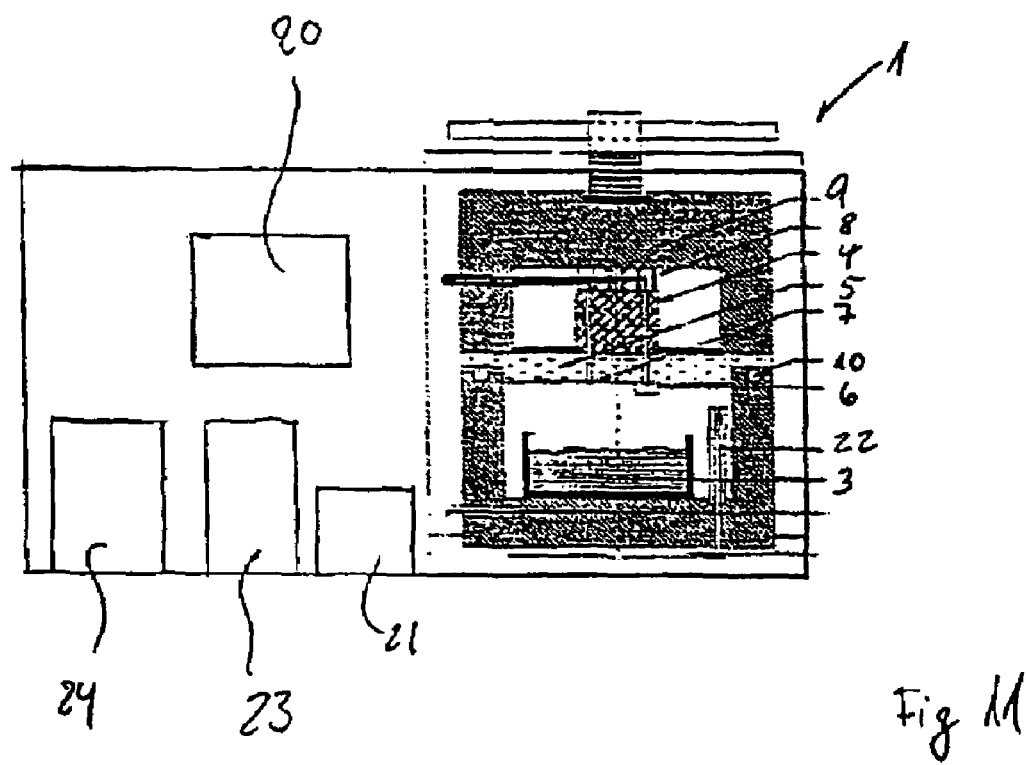
FIG. 11 illustrates a dew point meter according to one embodiment of the invention.

In FIG. 11 is illustrated a dew point meter 1 according to one embodiment of the invention. In addition to the features relating to the measuring procedure the dew point meter is supplied with a touch screen 20 on which status, results and RH development may be shown, and at the same time the touch screen may serve as an input means. A vacuum pump 21 is connected to an evacuation duct, such that a vacuum may be created in the measuring chamber. Furthermore an optionally rechargeable battery pack 23 is provided. The unit 1 is furthermore provided with a micro computer 24 for computing measurements received from the probes T1, T2 and storing said data.

DDA is a new measuring technique for determination of dew point temperature and relative humidity in closed systems; the DDA measuring technique is characterized as follows:

The dew point temperature, Td, is determined by dynamic measurement of shift of thermal boundary condition for a thermoelectric sensor, which is cooled.

The measurement of dew point temperature is directly related to the physical condensation phenomenon, which is to be determined, and not to indirect property changes in other coupled systems (change of resistance, capacitance, etc.).

The measurement of dew point temperature is only based on recording of a thermal effect and thus a simple temperature determination.

The sensor surface where condensation is registered when the dew point temperature, Td, is passed, is the thermoelectric junction point, i.e. the sensor surface is identical with the thermoelectric sensor point.

The sensor surface, where the onset of the dew point is registered, can be miniaturised so that the moisture interaction between a sample and the measuring system is minimal.

The dew point temperature, Td, is determined by extrapolating back to the time, where no moisture from the surroundings has condensed on the sensor surface; this eliminates the effect of interaction between sensor surface and the sample at the time Td is determined.

The dew point temperature in an advantageous embodiment is determined in a closed measuring cell, which has been evacuated for atmospheric air, so that the condensation rate is determined by pressure differences in an atmosphere of water vapour and not delimited by the molecular diffusion rate of water vapour through a dominating, inactive atmosphere.

These characteristics are the background for the unique features the DDA technique has compared with other measuring techniques, including:

The ERH determination is extremely precise. This is enabled through differential temperature measurement. With thermocouples a differential temperature of approximately 0.001° C. can be registered, whereas determination of absolute temperatures typically is within 0.1° C.

The repetitive accuracy is excellent and free of drift. This is a result of the DDA being based on a fundamental physical principle. Also minimal moisture interaction with the material sample ensures the accuracy of the technique.

The ERH determination is very fast. Evacuation of the measuring chamber ensures fast moisture equilibrium with the material sample, and the very small sensor surface, approximately 0.25 mm$^2$, provides immediate dew point identification.

The DDA instrument can perform ERH measurements up to 100%. Due to a slight overtemperature at the sensor surface, the instrument is capable of measuring the ERH of pure water.

The DDA technique is sturdy. The technique is based on simple thermocouple measurements, and the design of the instrument allows easy cleaning and maintenance.

Within research and development as well as industrial control of the quality and durability properties of products, measurement of the moisture condition of materials and substances plays a central role. The equilibrium moisture of substances and materials is a measure of the physical-chemical-water activity in the specimens. This is important for example with regard to:

Control of industrial desiccation processes.
Quality and durability evaluation of food and feedstock.
Control of storage of e.g. paper articles.
Tests of the service condition of building materials in structures.

To meet this basic need for measuring moisture, there are different electronic sensors based on measurement of indirect or temporary property changes in other systems e.g. change of electric conductivity or capacitance in a moisture-sensitive material. Basic problems with the measuring techniques used today are their operation, ageing and sensitivity to condensation.

It has been shown that the proposed measuring technique, which is based on recording of a basic, physical phenomenon, has quite unique stability and reproducibility properties to solve a number of specific measuring tasks.

The invention claimed is:

1. Device for determining the dew point temperature and relative humidity, wherein the device comprises a housing and wherein at least two thermocouples are provided inside said housing wherein at least a part of the interior of said housing constitutes a measuring chamber, and wherein one of the at least two thermocouples is shielded from exposure to the measuring chamber; wherein means are provided for changing the temperature of the thermocouples and registering the temperatures and/or the temperature difference between the at least two thermocouples;

wherein the thermocouples are arranged in a member exhibiting low thermal conductivity, for example a plastic member, so that only the tip of the thermocouples are exposed to the measuring chamber, of which one thermocouple is shielded; and wherein on the side of the member exhibiting low thermal conductivity not being exposed to the measuring chamber the thermocouples are encased in a heat conductive material and the means for changing the temperature comprising a heating and/or cooling element is arranged in connection with the encasing.

2. Device according to claim 1 wherein the measuring chamber is completely sealed off from the surrounding environment, and that a source of vacuum may be connected for evacuating the measuring chamber.

3. Device according to claim 1 wherein a thermocouple is provided for measuring the temperature of the housing.

4. Device according to claim 1 wherein the housing is made of two mutually fitting sections, which can be fitted in such a way that the measuring chamber, thermocouples, member exhibiting low thermal conductivity, encasement and heating/cooling element are comprised inside the housing, and wherein means are provided through the housing for connecting the thermocouples to said registering means, and the heating/cooling element to control means, and optionally the measuring chamber to a source of vacuum.

5. Device according to claim 1 wherein means for creating a dynamic gas flow around the thermocouples is provided, and wherein the housing is in open communication with the surrounding environment.

6. Device according to claim 1 wherein the device is a self contained unit comprising a source of power, means for registering, storing, computing and displaying measurements.

7. Device according to claim 1 wherein the member is made of plastic.

8. Device according to claim 1 wherein the heat conductive material is copper.

* * * * *